United States Patent [19]

Moeckl

[11] 3,955,285

[45] May 11, 1976

[54] DEVICE FOR MEASURING POSTURE-DETERMINING PARAMETERS OF A HUMAN BODY

[76] Inventor: Ernst Moeckl, Wangener Hohe-Durrbach 1, 7 Stuttgart-Wangen, Germany

[22] Filed: Sept. 9, 1974

[21] Appl. No.: 504,288

Related U.S. Application Data

[63] Continuation of Ser. No. 362,631, May 21, 1973, abandoned, which is a continuation of Ser. No. 30,906, April 22, 1970, abandoned.

[30] Foreign Application Priority Data

Apr. 24, 1969 Germany............................ 1920766

[52] U.S. Cl............................................. 33/174 D
[51] Int. Cl.²......................................... G01B 5/20
[58] Field of Search............... 33/2 R, 8, 174 D, 175

[56] References Cited

UNITED STATES PATENTS

| 324,022 | 8/1885 | Hand ...................................... 33/8 |
| 422,067 | 2/1890 | Bernheim................................. 33/8 |
| 1,092,737 | 4/1914 | Mead et al............................... 33/8 |
| 2,052,099 | 8/1936 | Lytton ..................................... 33/8 |
| 2,053,810 | 9/1936 | Bisel....................................... 33/2 R |
| 2,784,491 | 3/1957 | Sankey................................... 33/2 R |
| 2,818,648 | 1/1958 | Jochheim................................. 33/8 |

FOREIGN PATENTS OR APPLICATIONS

891,913 8/1953 Germany.......................... 33/174 D

*Primary Examiner*—Richard E. Aegerter
*Assistant Examiner*—Charles E. Phillips
*Attorney, Agent, or Firm*—Ernest G. Montague; Karl F. Ross; Herbert Dubno

[57] ABSTRACT

An upright column, rising from a base provided with a heel stop for a person standing thereon, carries five slides supporting respective feelers engageable with the body of that person for ascertaining body dimensions and posture. The feeler on the top slide measures the person's height. The next-highest slide carries two horizontally swingable and jointly tiltable feeler heads making three-point contact with the person's shoulders. The third slide carries a kyphosis feeler engaging an upper part of the spine. The fourth slide carries a lordosis feeler engageable with a lower part of the spine, the two last-mentioned feelers being interconnected by a linkage determining the degree of spinal curvature in the plane of symmetry of the body. The lowermost slide carries two feeler arms which are tiltable and relatively displaceable in a vertical plane on a swingable bar to determine the width and attitude of the pelvis. An ancillary feeler plate, mounted on a horizontally shiftable member supporting the feeler heads on the second slide, is engageable with the shoulder blades to establish a reference position for the shoulder measurements, this plate having a slot to accommodate the kyphosis feeler.

18 Claims, 13 Drawing Figures

DEVICE FOR MEASURING POSTURE-DETERMINING PARAMETERS OF A HUMAN BODY

This is a continuation of application Ser. No. 362,631, filed May 21, 1973, which is a continuation of my earlier application Ser. No. 30,906, filed April 22, 1970, both now abandoned.

My present invention relates to a device for measuring the human body more particularly for ascertaining various parameters relating to the posture of a person.

Conventional devices for measuring the height of the body include, for example, a feeler on the guided on an upright column and vertically displaceable along a scale graduated in units of length such as centimeters, thus providing direct readings of the height of the person to be measured after the feeler has been brought into contact with the top of the head of such person.

However, there is an additional need for means enabling individual parts of the human body to be measured in a simple and reliable manner, e.g. in order to determine postural damage. If certain measurements of a human body deviate from the determinable optimum values, such deviations, more often than not, are caused by postural weakness, postural deficiencies, or even postural damage. Posture in this sense is the totality of postural phenomena resulting from the cooperation of bones, muscles, and ligaments, essentially referred to the constitution of the spine. This concerns certain parts of the body, i.e. the position of the spine as viewed from the front and from the side as well as the positions of the shoulders, the pelvis, and so forth. Deviations of these anatomical parts from determined standard measurements of healthy people as a result of a deterioration of posture are indicative of certain weaknesses and pathological conditions. For example, the curvatures of the spine may be increased, which may lead to a hyperlordosis (hollow back) or a pronounced kyphosis (humpback). Furthermore, a swayback may develop as a result of stooping shoulders, especially in case of a diminishing tension in the shoulder muscles and a torsal slipping of the shoulder blades. This is usually accompanied by a lateral obliquity of the pelvis and an oblique position of the shoulders. Weaknesses of this nature may be corrected by suitable exercises, and it is a fact which deserves to be noted that people whose posture approaches an optimum are healthier and more resistive than people with postural weaknesses. The widespread present postural inadequacies have their causes in the modern way of life, which is characterized by a general lack of exercise and frequently leads to excessive weight.

It is the object of the present invention to provide a device of the type referred to above which is characterized by simplicity of construction and enables postural measurements of the aforedescribed kind to be taken in an uncomplicated manner.

In accordance with a feature of my present invention a lordosis feeler is disposed on a slide in a manner permitting it to be moved approximately perpendicularly with respect to an upright main guide, on which this slide is supported. This arrangement enables the feeler to be adjusted, in a simple manner, to the height of the apex of the lordotic curvature of the spine with the aid of the slide and provides a ready measurement of the height of that apex. Furthermore, the feeler may be brought into contact with the body in the region of the lordotic apex by displacing it with respect to the slide in a direction perpendicular to the main guide, so that the horizontal distance of the apex of curvature from a vertical baseline, defined by a heel stop, may be measured and the amount of lordosis may thus be determined.

Since postural damage may include lateral or scoliotic curving of the spine, an advantageous arrangement is one which permits the lordosis feeler to be moved with respect to the slide in two directions approximately perpendicular to each other and to the main guide so that the amount of scoliosis may be measured as well. In such an arrangement, the lordosis feeler may be supported, in a simple manner, on a rail with a screw spindle for horizontal adjustment of the feeler along a measuring scale; this rail, in turn, is supported on the slide in a manner permitting it to be displaced transversely to the spindle and the main guide, thus enabling the lordosis feeler to be accurately aligned with the spine of the subject.

Pursuant to another feature of the present invention, a similarly mounted feeler may be used to measure kyphosis by determining the distance of the apex of the kyphotic curvature from the baseline.

In a particularly advantageous embodiment of the invention, the lordosis feeler and the kyphosis feeler are connected to each other through a pivotal linkage whereby the position of the two feelers relative to each other and thus the shape of the spine within the range of these feelers may be readily determined with precision. If the pivotal linkage is connected to an angle-measuring instrument disposed on one of the feelers, preferably the lordosis feeler, the shape of the spine in that region will be indicated goniometrically.

In a simple embodiment of the invention, the pivotal linkage includes a link of variable length articulated to both feelers. Advantageously, this linkage comprises a bell-crank lever, one leg of this lever serving to connect the two feelers while its other leg carries a pointer enabling a direct reading of the angle of inclination existing between kyphosis and lordosis. The connecting leg of the pivotal linkage may take the form of a telescopic unit with a plurality of nested tube sections or with a traction member, such as a rope, that may be extracted from a tube so that a straight position of this connecting leg is ensured at all times.

Pursuant to a further feature of the present invention I provide another such feeler designed to engage the shoulder of the subject, this feeler being supported on its slide through the intermediary of a holder in a manner permitting it to be displaced in a plane approximately perpendicular to the main guide. Such a feeler can thus be used for measuring the stoop, height, and breadth of the shoulders. It is advantageous to provide two, preferably symmetrically disposed, shoulder feelers to enable both shoulders to be measured simultaneously.

To facilitate a stepless adjustment of the shoulder feelers in all directions in the horizontal plane, the shoulder feelers are supported on their holder in a manner permitting them to be pivoted with respect to a measuring scale or the like about a, preferably common, axis which is approximately parallel to the main guide. Measuring heads on the shoulder feelers may be slidably disposed preferably along a measuring scale, on swingable arms, so that a simple construction results.

In a preferred embodiment of the invention, each shoulder feeler, is designed as a bracket pivotable about an axis approximately perpendicular to the main guide whereby the two shoulder feelers may be tilted to assume different heights with respect to each other, thus enabling the obliquity of the shoulders to be determined. To provide a simple means for this purpose, an angle-measuring instrument is connected to the bracket, a pointer thereof being preferably disposed on the pivotal axis.

As subcutaneous fatty tissues or muscular systems in the region of the shoulders may interfere with the measurements, each measuring head is provided with several (preferably three), sensors gripping the shoulder, in the region of the acromion, from the rear, from the front and from above, thus ensuring an accurately determinable position of the measuring head in contact with the shoulder.

In a particularly advantageous arrangement the shoulder feeler is provided with an ancillary feeler which is preferably secured to the holder of the shoulder feelers and thus may be displaced only with respect to the associated slide, in a direction perpendicular to the main guide, without following the various pivoting motions of the shoulder feelers. With the aid of this ancillary feeler, the shoulder feelers may be moved to a basic measuring position relative to the subjects body, thus ensuring very accurate measurements of the shoulders, one measured parameter being the distance of the ancillary feeler from the baseline precise alignment is achieved if the ancillary feeler is arranged to contact the shoulder blades of the body to be measured. An advantageous arrangement is one in which the aligning feeler takes the form of a substantially vertical plate. To prevent this plate from restricting the movement of the kyphosis feeler there below, the plate is provided with a passage for the kyphosis feeler, preferably in the form of a slot open at the bottom and disposed parallel to the main guide.

A device according to the present invention may also comprise a pelvis feeler with two approximately parallel contact arms disposed on a slide supported on the main guide, these contact arms being displaceable transversely to their longitudinal directions and approximately perpendicularly to the main guide so that they may be used to measure the breadth and the height of the pelvis.

A particularly advantageous arrangement of this nature is one in which a holder carrying these pelvis-contacting arms is supported on the slide in a manner permitting it to be pivoted about an axis extending approximately symmetrically between the two contact arms and perpendicularly to the main guide, whereby also the obliquity of the pelvis can be measured directly. If the holder is connected to an angle-measuring instrument, preferably with a pointer swingable about the pivotal holder axis, the obliquity of the pelvis may be directly determined in angular degrees. Such a pelvis feeler is sturdy enough to avoid any deformation which would invalidate the measuring result.

If the slides of the several feelers are supported in a manner permitting them to be separately displaced, along the common main guide, each feeler may be accurately adjusted to the desired measuring height independently of the adjacent feeler.

I further prefer to provide means enabling each feeler to be locked in the position to which it has been adjusted so that a reading of the measuring results may be preserved directly on the device.

A locking arrangement of this type may, for instance, comprise clamping means for arresting the slide. A simple clamping means may be a screw with a manipulator which is preferably located at the back of the slide.

To provide direct readings of the height of each measuring point, e.g. with respect to the surface on which stands the person to be measured, the main guide is provided with a continuous measuring scale for the slides.

According to a further feature of the present invention, the main guide takes the form of an upright rail on which the slides are preferably detachably mounted. This enables the device according to the present invention to be optionally fitted with some or all of the slides described so that the device may be equipped with corresponding feelers to suit varying requirements.

With a guide rail of triangular cross-section, the slide can have bearings in contact with two surface of the rail and at least one thrust bearing in contact with the third surface thereof, this thrust bearing being adjustable transversely to the latter surface, thus enabling the slides to be supported in a simple fashion and in a manner which substantially eliminates play and prevents rotation. It has been found advantageous to provide two bearings each, e.g. ball bearings, located one above the other on the two first-mentioned surfaces of the triangular rail and a single thrust bearing on the third surface of that rail, this thrust bearing being preferably located at mid-height of the distance between the bearings disposed on the other two rail surfaces.

To obviate the need for detaching all other slides from the guide rail in order to remove one, each slide is split into two complementary bearing shells which embrace the guide rail and may be separated from each other.

Adjustment of the slide along the main guide may be very accurate if the slide is provided with a rotatably supported drive element connected to a manipulator and engaged by the main guide. This drive element may simply be a friction wheel, preferably in the form of a truncated cone, which contacts one of the surfaces of the triangular guide rail and whose shaft projects from the slide carry the manipulator.

It has also been advantageous to design at least one and preferably each feeler arm as a member of oblong, erect cross section which combines light weight with high strength, is gripped with ease, and may be supported in its respective slide by means of profiled rollers in a manner permitting it to be shifted safely and without rotation.

According to a further feature of the present invention, the rotatable drive element of at least one slide so engages the associated feeler arm that the feeler arm, too, may be shifted very accurately with respect to the associated slide by means of a micro-adjustment.

A convenient manipulation of the device results if the manipulator of the drive element engaging the feeler arm is disposed on a lateral surface of the slide, preferably on the side facing away from the manipulator for the friction wheel coacting with the main guide.

A measuring scale associated with a measuring mark on the respective slide may be provided on the lateral surface of at least one feeler arm, especially if the same has an oblong cross section. If all measuring scales are disposed essentially adjacent one another, preferably in the region of the main guide, all essential measurements may be read from one position.

To enable the height of the body to be measured, too, another slide-mounted feeler may be shiftably supported on the main guide.

A considerable simplification in the use of the measuring device according to the invention results if at least one feeler, preferably the lordosis feeler and the kyphosis feeler, is spring-loaded in the direction of body contact so that the feeler is pushed back to the measuring position by the subject's body against the spring force when the subject is stood against the device and no specific actuation of the feelers is required. Operation of the measuring device may also be simplified by an arrangement in which at least one feeler, preferably the shoulder feeler, the pelvis feeler and the height-measuring feeler, is spring-loaded in the direction of an initial limiting position so that these feelers may be released after the respective measurement has been taken and automatically return to their initial positions. It is also possible to spring-load the shoulder feeler or the pelvis feeler in such a manner that it will automatically return to a horizontal initial position by swinging about its pivotal axis.

An advantageous spring-loading arrangement is one in which a spring, preferably a tension spring, is disposed inside the respective feeler arm for protection. The springs for the height-measuring feeler are advantageously disposed inside the guide rail, preferably in a manner permitting these springs to be adjusted in length, so that the tension springs may be moved together with their feelers to a lower portion of the guide rail for measuring a group of short persons, e.g. children.

A weighing scale for determining the weight of the body may be provided at the foot plate of the device. As the tread plate of body-weighing scales is frequently displaced by less than 1 mm, the tread plate of the weighing scale may simultaneously serve as the base on which the subject stands while the measurements are being taken. If it be desired to eliminate the influence of such displacement on the results of the other measurements, the weighing scale may be provided with two tread plates disposed alongside each other, a stationary base surface being provided between the two tread plates. In this case, the person to be measured stands on the tread plates while the weight of the body is determined and on the stationary base surface while the other measurements are being taken. Advantageously the stationary base surface of the device, carries the aforementioned heel stop preferably provided with a centrally disposed centering web, so that an accurately definable standing position may be assumed with respect to the device without exercising special care. To ensure a reliable mounting for the individual feelers if they are of small dimensions, the guide rail is laterally offset with respect to the centering web, the bearing for reception of the feeler arm being provided on that side of the respective slide which faces the centering web.

When measuring a large number of persons it may be advantageous if at least one feeler is supported in a manner permitting it to be displaced by motor power, e.g. by means of electromagnets, pressure cylinders or the like, so that the feeler or feelers may be automatically moved to their positions of body contact whereupon all measurements may be determined. Especially in this case, it is also desirable to connect at least one feeler to a register serving to store the measured value for later evaluation. Such a register may be provided with a program by means of which the therapy corresponding to the respective postural damage is indicated, e.g. in the form of a printed enumeration of the exercises required.

Advantageously, a device embodying my present invention, is disposed in a housing with preferably detachable walls carrying charts and diagrams designed to teach its proper use. An advantageous arrangement is one in which a cabinetlike box is erected around the base plate of the device, the solid walls of that box having the same height as the guide rail. This box is closed by a lid at the top and by the base plate of the measuring device at the bottom. In addition, the box is provided with a lock and may be constructed in a manner permitting it to be used as a transport crate. The inner wall surfaces of the box are provided with full-scale illustrations demonstrating the individual measuring procedures - in particular the manipulations involved - in a clear manner. Before the measuring device is placed in use, the cabinetlike enclosure may be unlocked and swung open on hinges interconnecting the sidewalls of the box and then erected in the immediate vicinity of the device in a position affording rapid orientation about the use of the device.

The box may be of compact construction, e.g. in the form of a portable case, if the guide rail is assembled from two or more plug-type and/or telescoping sections.

The device according to the present invention may be put to many different uses. For example, it may be employed by physical-training instructors or by sports physicians, in sport schools, sports clubs, medical institutions or physical-training facilities, by general practitioners or orthopaedists, in hospitals or sanatoria, with the armed forces and the police force, in private homes or the like. If deviations from an optimum standard have been determined with the aid of the measuring device, suitable exercises for improvement may be determined and recommended, the device enabling the body to be measured and re-measured and the success of such exercises to be evaluated on the basis of the measuring results.

In the following, the invention will be described in greater detail, reference being made to the accompanying drawing showing an embodiment of the invention by way of example with the essential parts thereof represented approximately true to scale.

Figure 1:
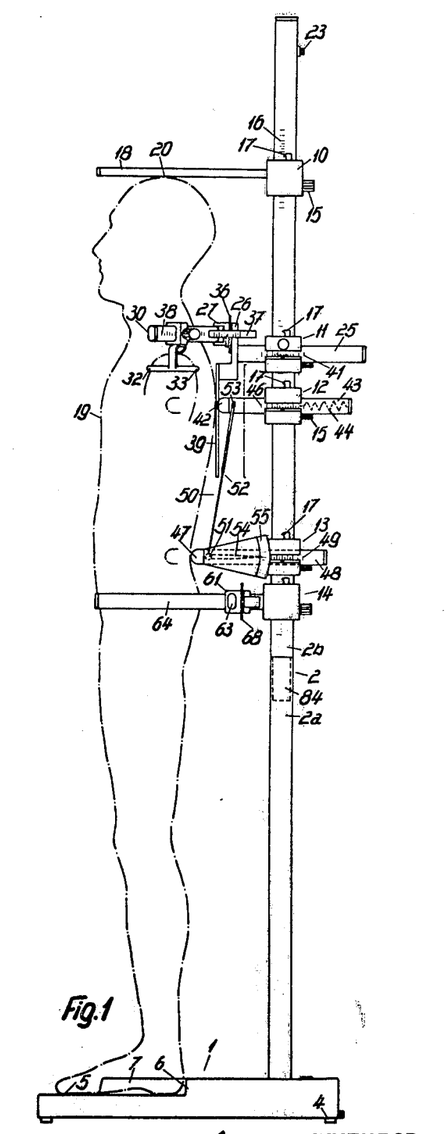
FIG. 1 is a side elevation of a device according to the invention.
Figure 2:
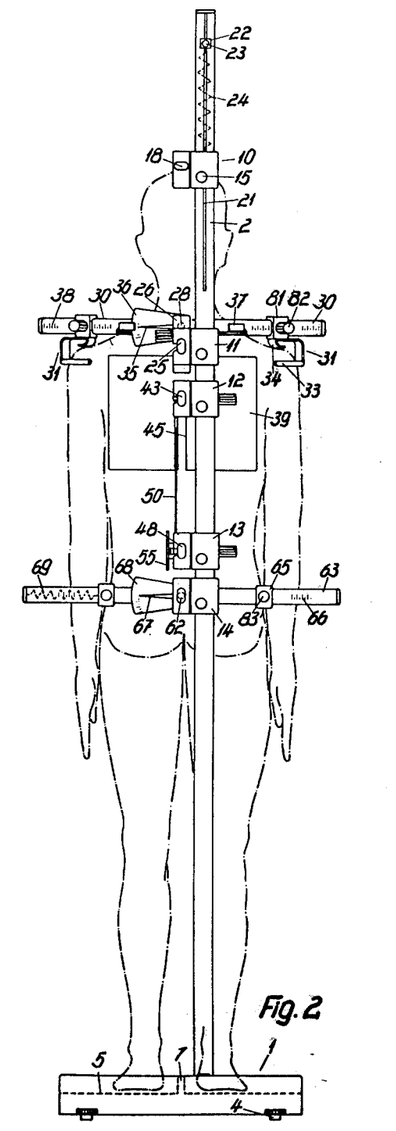
FIG. 2 is a rear elevation of the device according to FIG. 1.
Figure 3:
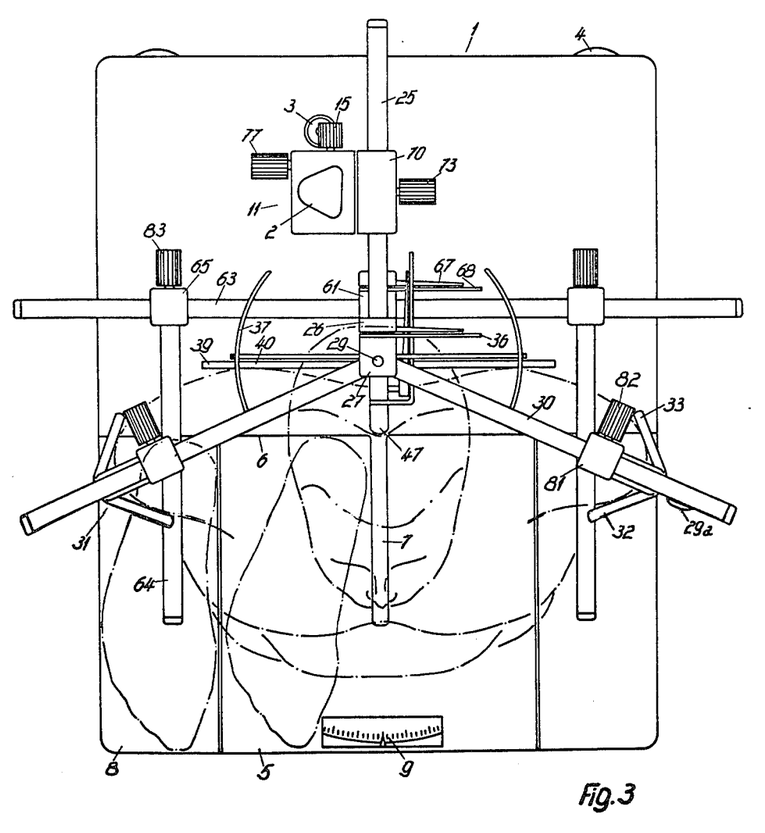
FIG. 3 is a top plan view of the device.

As may be noted from FIGS. 1 to 3, a device for measuring the human body in accordance with the present invention conprises a base 1 with a vertical guide rail 2 of approximately 2 m height attached to the rear portion thereof. The guide rail 2 is tubular and has a cross-section in the shape of an equilateral triangle with rounded corners. A spirit level 3 for accurate vertical positioning of the guide rail 2 is provided directly behind the latter at the top of the base 1. This positioning is effected by means of two vertically adjustable feet 4 provided on the underside of the rear portion of base 1.

A stepping surface 5 in the form of a depression in the base 1 is provided in front of the guide rail 2. The width of the stepping surface 5 is slightly more than twice the breadth of a human foot, this surface 5 being bounded at the rear by an approximately vertical heel stop 6 integral with a centering web 7 projecting perpendicularly from surface 5 and from step 6 in their plane of symmetry.

Two tread plates 8 of a body-weighing scale, disposed in the casing-shaped base 1 and not shown in detail, are provided on opposite sides of the standing surface 5, the width of each tread plate approximately corresponding to the breadth of a human foot. A dial 9 of the body-weighing scale is disposed in the front portion of stepping surface 5 for each reading.

The guide rail 2 supports five slides 10 to 14 of essentially similar construction disposed one above the other in a manner permitting these slides to be separately shifted, each slide being lockable with respect to guide rail 2 by means of a manipulator 15. On one of its plane lateral surfaces extending in the longitudinal direction, the guide rail 2 is provided with a length-measuring scale 16 drawn with reference to the stepping surface 5. Within the range of this length measuring scale, which may be formed by a measuring tape glued to the rail, each slide is provided with a pointer 17 providing direct readings of the distance between the measuring point of the respective slide and the stepping surface 5.

The top slide 10 carries a body-height-measuring feeler 18 in the form of a horizontally projecting cantilever-type arm which is rigidly connected to the slide 10. When brought into contact with the top of the head 20 of a person 19 represented by dash-dot lines in FIGS. 1 to 3, the feeler 18 provides a direct reading of the height of that person. In the range of the slide 10, the back of the guide rail 2 is provided with a longitudinal slot 21 engaging a corresponding projection of this slide. Above the slide 10, a retainer 22 is supported in a manner permitting it to be shifted along slot 21 in the guide rail 2 and to be locked by means of a fastener 23, this retainer 22 also having a projection engaged by the slot 21. A tension spring 24 located in the guide rail 2 is anchored to the projections of the retainer 22 and the slide 10 so that the height-measuring feeler 18 is biased in the direction of its upper limiting position. To measure the height of comparatively short persons, the retainer 22 can be shifted downwardly. To take the measurement, the feeler 18 is moved down against the slight force exerted by the tension spring 24 and brought into contact with the top of the head 20 of the person 19 to be measured. If the measurement thus taken is immediately read on the measuring scale 16, the feeler may be released again as soon as such reading has been taken and will then automatically be returned by the spring to its initial position. Alternatively, the slide 10 may be locked in its measuring position by actuating the manipulator 15 so that a measurement may be retained for a prolonged period of time. The construction of the slide 10 may be simpler than that of slides 11 to 13 described below.

The second slide 11 carries a feeler-supporting arm 25 in a manner permitting that arm to be displaced in a direction perpendicular to the guide rail 2 and parallel to the centering web 7. One end of the feeler arm 25 carries a holder 26 which supports a bracket 27 in a manner permitting same to be tilted about a horizontal pin 28 disposed parallel to the centering web 7. The bracket 27 supports two arms 30 disposed in the form of a V with an obtuse vertex angle in a manner permitting these arms to be separately pivoted about a common pin 29 disposed parallel to the guide rail 2 and symmetrically with reference to the standing surface 5. Each arm 30 has mounted thereon a shoulder-measuring feeler head 31 in a manner permitting the head to be shifted longitudinally. Each feeler head 31 is provided with three sensing pins 32 to 34 located at the corners of an imaginary triangle; on being brought into contact with the shoulder of the person 19 in the region of the acromion, one sensing pin 32 contacts the shoulder at the front, the opposite sensing pin 33 contacts the shoulder at the rear, and the third pin 34 overhanging the other two sensing pins contacts the shoulder on the top, the three pins being part of a unitary clip. As shown in FIG. 3, the two sensors 32, 33 are formed as round bars disposed approximately at right angles to each other, these bars straddling the shoulder of subject 19. The feeler heads 31 are brought into contact with the shoulders of the body 19 by being so turned about the pins 28 and 29 and displaced with respect to the swingable arms 30 that their pins 32 to 34 contact the shoulder in the manner described. The pivot pin 29 of the bracket 27 is the fulcrum of a printer 35 associated with a goniometric scale 36 secured to the holder 26 so that the tilting angle of the bracket 27 and thus the difference in height between the two feeler heads 31, i.e. the obliquity of the shoulder, may be directly read in angular degrees. Alternatively, the scale 36 may be secured to the pivot pin 28 and the pointer 35 to the holder 26. Each swing arm 30 coacts with a measuring scale, e.g. in the form of a bent strip 37, curved about the pivot pin 29 and secured to the bracket 27 to permit the stoop of the shoulders, i.e. the horizontal distance between the shoulders and the back, to be determined. In addition, each swing arm 30 is provided with a length-measuring scale 38 for measuring the distance by which the feeler head 31 has been displaced along the arm. Advantageously, in the region of one measuring head 31, a manipulator 29a is slidably supported on the corresponding arm 30 in an easily accessible position, this manipulator being connected to a clamp for locking the swing arm with respect to the pivot pin 29 through a linkage not shown in detail which is accommodated in that arm 30. Furthermore, the holder 26 carries an ancillary feeler 39 in the form of a vertical plate made of transparent material, the plate 39 serving to align the shoulder-measuring assembly with the person 19 so as to bring this assembly into a reference position switchable for the measurements. The elevation of the plate 39 may be adjusted to bring the plate 39 at least approximately into contact with the shoulder blades 40 of the person 19. The distance by which the shoulder-measuring assembly must be displaced with respect to the slide 11 toward the person 19, in a direction perpendicular to the guide rail 2, in order to accomplish this adjustment may be read directly on a measuring scale 41 disposed on the lateral surface of the feeler arm 25, this scale coacting with a corresponding measuring mark on the slide 11. The pointer 17 disposed on the slide 11 enables the height of the shoulder to be read directly on the scale 16. To take a measurement, the shoulder-measuring assembly may initially be arranged close enough to the rail or guide column 2 to prevent the shoulders of the person 19 from contacting the feeler plate 39 when that person's feet are in contact with the stop 6, otherwise the body might be brought into, and kept in, an unnaturally inclined position by plate 39.

After the person to be measured has assumed a natural position, the feeler plate 39 is carefully moved onto the shoulder blades 40 and then locked with respect to the slide 11 in a position where this plate is in light contact with the shoulder blades, whereupon the complete procedure for determining the measurements of the shoulders may be carried out. After the measurements have been read, the shoulder-measuring assembly is returned to its initial position, the feeler plate 39 assuming, for example, the retracted position indicated by the dash-dot lines in FIG. 1. Return to the initial position may be effected automatically by suitable means, upon release of the locking mechanism. For example, a spring which retracts the shoulder-measuring assembly toward the slide 11 may be disposed in the feeler arm 25, this spring being connected to the arm 25 at one end and to the slide 11 at the other end. Alternatively, the spring may be disposed so that the feeler plate will be biased in the direction of body contact and pushed back when the person is stood against the device. The slide may be spring-loaded in the upward direction in a manner corresponding to that provided for slide 10 so as to be automatically moved upwardly after the shoulders have been measured. Furthermore, the bracket 27 may be spring-loaded in such a manner as to be automatically pivoted about the pin 28 into a position where the arms 30 are horizontal.

A kyphosis feeler 42 with a contact arm 43 is slidably supported on the slide 12 below the slide 11, the centerline of the arm 43 being located in the midplane of the centering web 7 which is offset from column 2. The contact arm 43 accommodates a tension spring 44 acting in a direction opposite that of the biasing spring of the feeler arm 25, the tension spring 44 being connected to the contact arm 43 at one end and to the slide 12 at the other end, so that the kyphosis feeler 42 will be urged toward the body 19 to be contacted. To measure the body 19, the slide 12 is so adjusted in height that the feeler 42 will be located between the shoulder blades 40 approximately at the apex of the kyphotic curvature. For unrestricted movement of the feeler 42 the plate 39 is provided with a vertical slot 45, open at the bottom, in which the feeler 42 can be moved without hindrance. The height of the kyphosis may be directly read on the scale 16 with the aid of the pointer 17 provided on the slide 12. In addition, the horizontal distance of the kyphosis, e.g. from the heel stop 6 and-/or the feeler plate 39, may be determined on a scale 46 provided on the arm 43.

Similarly to the arrangement provided for the slide 12, a contact 47 with a feeler arm 48 is slidably supported on the slide 13 below the slide 12 in a manner permitting the feeler 47 to be displaced horizontally and parallel to the feeler 42, the feeler 47 serving for the measurement of lordosis and being positionable at the level of the apex of the lordotic curvature by shifting the slide 13 so that a direct reading of this level is provided by the pointer 17 disposed on the slide 13. In addition, the horizontal distance of the apex of the lordosis, e.g. with respect to the heel stop and/or the feeler plate 39, may be determined with the aid of a scale 49 provided on the feeler arm 48.

As is also apparent from FIG. 1, a bell-crank lever 50 is connected to the lordosis measuring arm 48 in a manner permitting the lever 50 to be pivoted about a horizontal pin 51 disposed perpendicular to the direction in which the feeler 47 may be displaced, one leg 52 of the lever 50 being pivotably connected to the feeler arm 43. The leg 52 is adjustable in length so that it will automatically adapt itself to the distance between the feeler arms 43, 48. The distance between the pivot pin 51 and the tip of lordosis feeler 47 is the same as that between the point of articulation 55 of the leg 52 to the contact arm 43 and the tip of kyphosis feeler 42. The free end of the other leg 54 of the bell-crank lever 50 forms a pointer associated with a gonimetric scale 55 on the slide 13 for direct readings of the angle between the apex of the kyphosis and the apex of the lordosis. In the same manner as the feeler arms 25, 43, the feeler arm 48 is spring-biased in the direction of body contact of the lordosis feeler 47 with respect to the slide 13. The linkage 50 – 53 thus indicates the degree of curvature of the spine in the plane of symmetry of body 19, as represented by the tilt angle of the extensible link 52.

Figure 8:
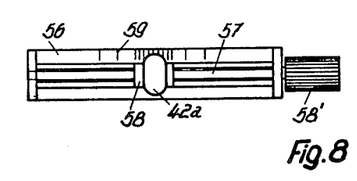
FIG. 8 is a front elevation of a further embodiment of a lordosis or kyphosis feeler.
Figure 9:
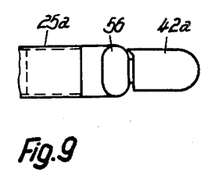
FIG. 9 is a side elevation of the feeler according to FIG. 8.
Figure 10:
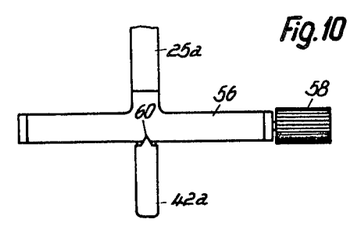
FIG. 10 is a top plan view of the feeler according to FIG. 8.

Alternatively, the kyphosis-measuring means and the lordosis-measuring means of the device according to the present invention may take the form represented in FIGS. 8 to 10 for the kyphosis feeler 42a. According to FIGS. 8 to 10, the free end of the feeler-supporting arm 25a has attached to it a transverse horizontal extension in the form of a rail 56 supporting a screw spindle 57 extending in the longitudinal direction of rail 56, the screw spindle 57 being rotatable by means of a manipulator 58'. The feeler 42a is slidably supported on the rail 56 and engaged by the spindle 57 through a nut 58. The rail 56 is provided with a length measuring scale 59 coacting with a pointer 60 on the feeler 42a. This arrangement enables the feeler 42a to be accurately aligned with the center of the spine, even in the case of lateral or scoliotic deformation, and the lateral deviation to be read off with the aid of the scale 59.

To take a measurement with the aid of the feelers 42, 47, the person 19 steps onto the standing surface 5, the two feelers 42, 47 being pushed back against the force of their biasing springs as soon as the person 19 assumes his natural posture. Both feelers 42, 47 are then vertically adjusted along the guide rail 2 and moved to the desired measuring position. To immobilize the feeler arms 43, 48 with respect to the corresponding slides 12 and 13, respectively, these slides may be provided with suitable locking devices, e.g. clamping screws.

The slide 14 supports a bracket 61 in a manner permitting same to be tilted about a pivot pin 62 disposed parallel to, and in the vertical midplane of, the pivot pin 28 of the shoulder-measuring assembly, the bracket 61 carrying a horizontal bar 63 Arms supports two pelvis-contacting arms 64 provided with sliders 65. Arms 64 are parallel to the feeler arms 43, 48 and can be displaced and locked with reference to a length-measuring scale 66. The pelvis contacting arms 64 are placed against, or on, the hip bones of the body 19 to be measured so that the height of the pelvis may be read with the aid of a pointer provided on the slide 14 while the breadth of the pelvis may be read on the transverse scale 66 of the bar 63. The pivot pin 62 is the fulcrum of a pointer 67 coacting with a scale 68 secured to the slide 14 so that the obliquity of the pelvis may be directly read in angular degrees on that scale 68. The bracket 61 is spring-loaded in such a manner that the bar 63 will be automatically returned to a horizontal position by being pivoted about the pin 62.

The bar 63 houses tension springs 69 which are connected to it at one end and to the adjacent slider 65 at the other end, whereby the sliders 65 and thus the feeler arms 64 are urged toward the adjacent ends of the bar 63 and are automatically returned to an initial position in the unlocked condition. A resetting spring for horizontal positioning of the bar 63 may be provided by a similar arrangement.

As all measuring scales are disposed on or in the immediate vicinity of the guide rail 2, all measurements taken may be read essentially from one position. The feelers 18, 64 and the contact arms 25, 43, 48, the swing arms 3 and the bar 63 are formed from generally similar tubular members of oblong cross-section; except in the case of the height-measuring feeler 18, these cross-sections are erect so that measuring scales may be provided in plain view and in a simple manner on the lateral surfaces of the members. The oblong section of the height-measuring feeler 18 is horizontally disposed in order to provide a wide measuring surface.

The feeler 18, the contact arms 25, 43, 48, and the pivot pin 62 of the pelvis feelers 64 are disposed symmetrically with reference to a common, vertical midplane laterally offset from the guide rail 2, this midplane bisecting the centering web 7. This arrangement enables the aforementioned elements to be mounted laterally on the slides 10 to 14 and to be slidably constructed. The guide rail 2 is offset with respect to the centering web 7 to a corresponding extent.

Figure 4:
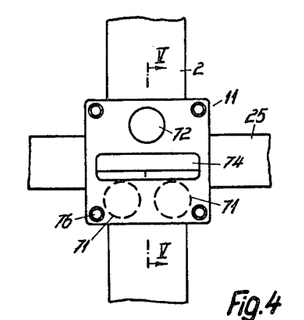
FIG. 4 shows a slide drawn to a larger scale.
Figure 5:
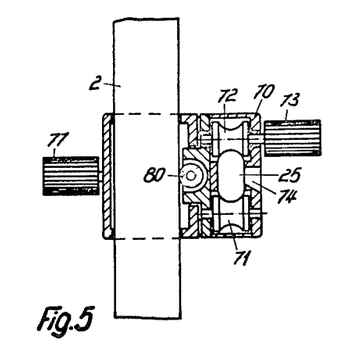
FIG. 5 is a section taken along the line V—V of FIG. 4.
Figure 6:
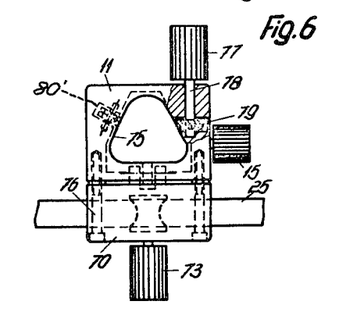
FIG. 6 is a top plan view of the slide according to FIG. 4.

FIGS. 4 to 6 show details of the slide 11 whose construction is similar to that of the slides 12, 13. On one of its lateral surfaces, the slide 11 is provided with a detachable housing 70 for supporting the feeler arm 25. Housing 70 accommodates two lower profiled rollers 71 with parallel axles to guide the lower longitudinal edge of the feeler arm 25 and a profiled friction roller 72 engaging the upper longitudinal edge of arm 25, friction roller 72 being disposed between and above supporting rollers 71. Friction roller 72 may be rotated by means of a manipulator 73 carried on its shaft projecting from the housing 70; this arrangement could also be inverted. The feeler arm 25 may be accurately adjusted by turning the manipulator 73. A window 74 on the housing 70 has an inclined lower boundary provided with the measuring mark associated with the scale 41 (FIG. 1).

The slide 11 is provided with an opening 75 conforming to the approximately equilaterally triangular cross-section of the guide rail 2, two ball bearings, disposed one above the other, are provided at each of the wall surfaces of opening 75 one such bearing has been shown at 80' in FIG. 6. A single ball or roller bearing, 80 disposed at mid-height of the vertical distance between the other ball bearings, is provided as a thrust bearing at the third lateral surface, i.e. the surface facing the housing 70, said single ball bearing being retained on the housing 70. The housing 70 may be adjusted with respect to the slide 11 by means of screws 76 so that the ball or roller bearing 80 retained by the housing 70 may be adjusted with respect to the corresponding surface of the triangular guide rail 2 in order to adjust the bearing play. The manipulator 15 of the locking device is disposed at the back of the slide 11, said locking device taking the form of a clamping screw which may be locked against the guide rail 2.

A further manipulator 77 is provided at the side of the slide 11 facing away from the manipulator 73 of the friction roller 72, the shaft 78 of said manipulator 77 in said slide 11 mounting a friction wheel 79 in the form of a truncated cone, said friction wheel 79 bearing as a drive means against the corresponding longitudinal surface of the guide rail 2. The height of the slide 11 may thus be micro-adjusted with respect to the guide rail 2 by turning the manipulator 77. Accordingly, the manipulators 15, 73, 77 are located on three mutually orthogonal surfaces of the side 11.

Figure 7:
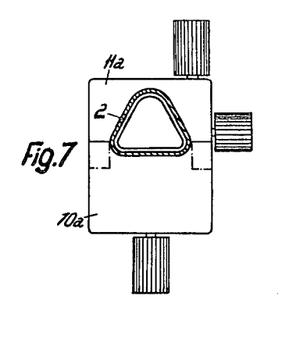
FIG. 7 shows a further embodiment of a slide in a representation according to FIG. 6.

In the embodiment of the invention shown in FIG. 7, the slide 11a and the housing 70a are separated to form two bearing shells which embrace the guide rail 2 and may be detached from each other and then removed from the guide rail 2 in a direction perpendicular to its longitudinal centerline.

As indicated by dash-dot lines in FIG. 7, the housing 70a may alternatively be provided with a projection which may be inserted into the slide 11a in a centered position and then forms one of the two bearing shells.

On the slides 10 and 14, the housings 70 serve as rigid supports for the feeler 18 and for a bearing for the bracket 61, respectively, the rollers 71, 72 being omitted in these instances.

Sliders 81, by means of which the shoulder-measuring feeler heads 31 are slidably supported on the swing arms 30, may also be locked in position by means of clamping screws 82. Corresponding locking screws 83 are also provided on the sliders 65 of the feeler arms 64.

Advantageously, the tubular members accommodating the several biasing springs are provided with longitudinal slots not shown, preferably at their longitudinal bottom edges. This slot, e.g. in the case of the feeler arm 43, guides a web of the associated slide 12 to which the corresponding end of the associated spring 44 is connected.

As is also apparent from FIGS. 1 and 7, the guide rail 2 may be of divided construction, comprising, for example, a lower portion 2a rigidly connected to the base 1 and an upper portion 2b inserted into the lower portion 2a with a corresponding projection 84 in a manner preventing rotation, the two portions 2a, 2b having the same outer cross-section. A suitable arrangement is one in which all portions of the guide rail have the same length. When not in use, all slides 10 to 14 may be moved down onto the lower portion 2a, whereupon the upper portion or sections 2b may be detached and inserted, for example, into openings provided for the purpose in the base plate 1 in a position parallel to portion 2a. As an alternative to the plug-type connection of the individual portions of the guide rail 2, the latter 2 may be composed of a plurality of telescoping portions, in which case it is advisable to ensure that the cross-section of each lower telescoping portion is smaller than that of the next higher telescoping portion.

Charts may be provided for evaluation of the measurements taken.

Figure 11:
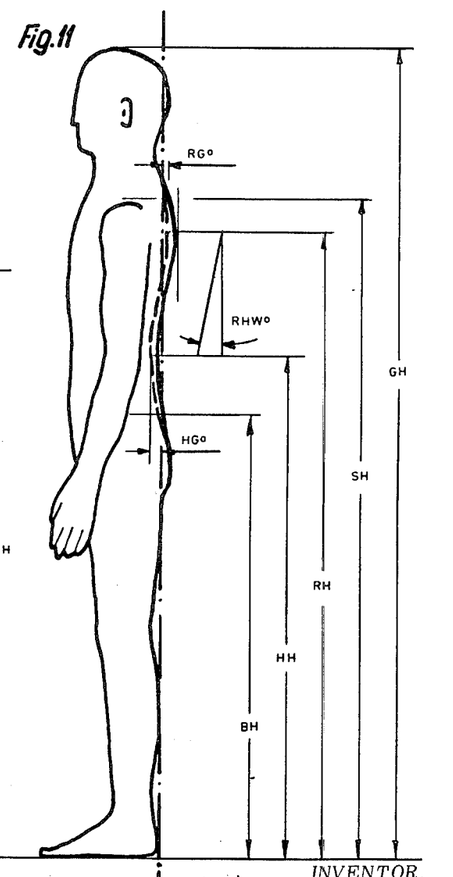
FIGS. 11 to 13 are a side elevation, a rear elevation and a top plan view, respectively, of a human body including indications of the various measurements that may be taken with the device according to the invention.
Figure 12:
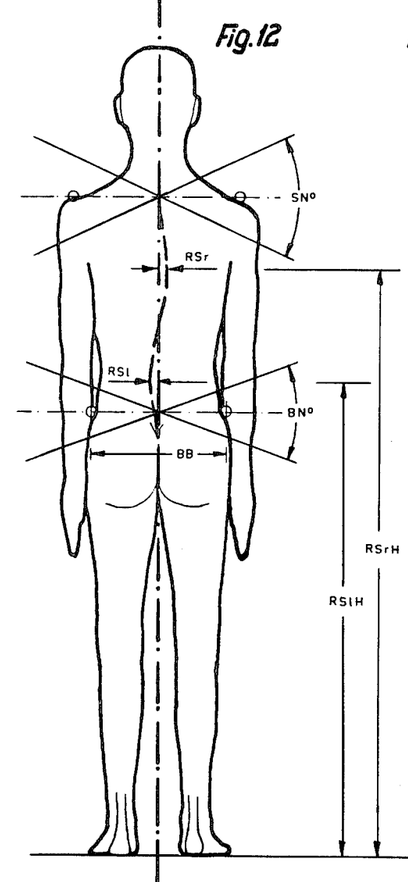
Figure 13:
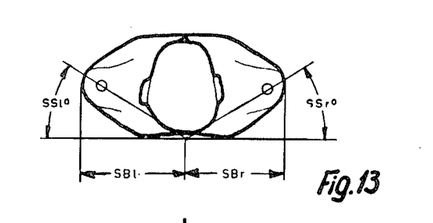

The device according to the present invention provides for determination of the measurements indicated in FIGS. 11 to 13, in which the various abbreviations have the following meanings assigned to them:

| | |
|---|---|
| GH | height of body |
| SHm | height of shoulder, center |
| SBr | breadth of shoulder, right |
| SBl | breadth of shoulder, left |
| SSr° | position of shoulder, right |
| SSl° | position of shoulder, left |
| SN° | drop of shoulder |
| RH | height of sway-back |
| HG° | curvature of sway-back |
| HH | height of hollow back |
| HG° | depth of hollow back |
| RHW° | kyphosis-lordosis angle |
| BH | height of pelvis |
| BB | breadth of pelvis |
| BN° | obliquity of pelvis |
| RSr | deviation of the spine (scoliosis) toward the right |
| RSrH | height of this deviation, right |
| RSl | deviation of the spine (scoliosis) toward the left |
| RSlH | height of this deviation, left. |

In particular for mass measurements, the device according to my invention may be designed so that, after the person to be measured has assumed a clearly defined position and tries to stand as natural and relaxed as possible, the measuring feelers are automatically brought up against the selected measuring points on the body and then come to rest at those points. In this case, the measuring feelers, rather than contacting the body, should be stopped at a distance of a few tenths of a millimeter by means of suitable switching elements. The measurements taken may then be registered automatically and comments issued, whereupon the various measuring feelers are returned to their initial positions, thus establishing the initial condition for measuring the next person.

While I have disclosed a preferred embodiment of the present invention, it is to be understood that the same is given by way of example only and not in a limiting sense.

I claim:

1. A device for measuring posture-determining parameters of a human body, comprising:
   a base forming a stepping surface for a person to be measured;
   an upright column rising from said base;
   a plurality of vertically displaceable slides carried at different levels on said column and including a lower slide, a higher slide and a further slide above said higher slide;
   feeler means mounted on said slides for engagement with the body of a person standing on said stepping surface, said feeler means including a pair of shoulder feelers mounted on said further slide with freedom of movement in a substantially horizontal plane on opposite sides of the plane of symmetry of said body, a kyphosis feeler on said higher slide, and a lordosis feeler on said lower slide, said kyphosis and lordosis feelers being movable transversely to said column for contact with an upper and a lower region of the spine of said body, respectively;
   a linkage interconnecting said kyphosis and lordosis feelers;
   a member supported on said further slide for substantially horizontal movement in said plane of symmetry;
   a holder pivotally secured to said member for rotation about a substantially horizontal axis in said plane of symmetry;
   an ancillary feeler including a substantially vertical plate provided with a downwardly open slot accommodating said kyphosis feeler, said ancillary feeler being carried on said member for engagement with the shoulder blades of said person to establish a reference position for said member; and
   an indicator coupled with said linkage for determining the curvature of the spine in the plane of symmetry of said body;
   said shoulder feelers including a pair of swingable arms pivoted on said holder and a pair of measuring heads carried on the extremities of said arms, each of said measuring heads including a plurality of sensors for simultaneous engagement of a shoulder of said person at different points.

2. A device as defined in claim 1 wherein said base is provided with a heel stop for the person standing on said stepping surface, at least one of said feelers being provided with scale means for measuring the distance of the contacted part of the spine from a baseline defined by said heel stop.

3. A device as defined in claim 1 wherein said linkage comprises an extensible link articulated to kyphosis and lordosis said feelers, said indicator including a pointer coupled with said link.

4. A device as defined in claim 1, further comprising a supporting arm movably mounted on said higher slide, said arm being provided with a transverse horizontal extension, said kyphosis feeler being mounted on said extension for displacement perpendicular to said arm.

5. A device as defined in claim 4 wherein said extension is provided with a screw spindle engaging said kyphosis feeler for controlledly displacing same.

6. A device as defined in claim 1 wherein the sensors on each of said measuring heads comprise three unitarily interconnected pins including two angularly adjoining shoulder-straddling pins and an overhanging third pin.

7. A device as defined in claim 1 wherein said slides include a lowermost slide, said feeler means further comprising a pair of pelvis feelers mounted on said lowermost slide with freedom of movement in a vertical plane perpendicular to said plane of symmetry.

8. A device as defined in claim 7, further comprising a holder for said pelvis feelers supported on said lowermost slide for substantially horizontal movement in said plane of symmetry and a transverse bar pivotally secured to said holder for swinging in said vertical plane, said pelvis feelers being shiftably mounted on opposite extremities of said bar.

9. A device as defined in claim 1 wherein said slides include a topmost slide, said feeler means comprising a length-measuring feeler carried on said topmost slide for engagement with the head of said person.

10. A device as defined in claim 9 wherein said column is provided with vertically shiftable anchor means for said topmost slide and with locking means for immobilizing said anchor means on said column, further comprising spring means secured to said anchor means and to said topmost slide for holding the latter at an elevated level above the head of said person.

11. A device as defined in claim 1 wherein at least one of said lower and higher slides is split into complementary portions embracing said column, said portions being detachable from each other.

12. A device as defined in claim 11 wherein said column comprises a rail of generally triangular cross-section, one of said portions being provided with first bearing means engaging two sides of said cross-section, the other of said portions being provided with a thrust bearing acting upon the third side of said cross-section.

13. A device as defined in claim 12 wherein said one of said portions is further provided with locking means for immobilizing the split slide with reference to said column.

14. A device as defined in claim 12 wherein said one of said portions is provided with drive means engageable with said one of said two sides for displacing the split slide along said column.

15. A device as defined in claim 14 wherein said drive means comprises a frustoconical friction roller.

16. A device as defined in claim 14 wherein said feeler means comprise a substantially horizontally movable holder mounted on said other of said portions, the latter being provided with manipulating means for displacing said holder.

17. A device as defined in claim 1 wherein said base is provided with an upstanding centering web in said plane of symmetry, said column being laterally offset from said centering web.

18. A device for measuring posture-determining parameters of a human body, comprising:

a base forming a stepping surface for a person to be measured;

an upright column rising from said base;

a plurality of vertically displaceable slides carried at different levels on said column and including a lower slide, a higher slide and a topmost slide;

feeler means mounted on said slides for engagement with the body of a person standing on said stepping surface, said feeler means including a length-measuring feeler carried on said topmost slide for engagement with the head of said person, a kyphosis feeler on said higher slide, and a lordosis feeler on said lower slide, said kyphosis and lordosis feelers being movable transversely to said column for contact with an upper and a lower region of the spine of said body, respectively;

a linkage interconnecting said kyphosis and lordosis feelers; and an indicator coupled with said linkage for determining the curvature of the spine in the plane of symmetry of said body;

said column being provided with vertically shiftable anchor means for said topmost slide and with locking means for immobilizing said anchor means on said column, further comprising spring means secured to said anchor means and to said topmost slide for holding the latter at an elevated level above the head of said person.

* * * * *